(12) United States Patent
Uhde

(10) Patent No.: US 12,262,953 B2
(45) Date of Patent: Apr. 1, 2025

(54) DETERMINING AN AVOIDANCE REGION FOR A REFERENCE DEVICE

(71) Applicant: Brainlab AG, Munich (DE)

(72) Inventor: Jörg Uhde, Munich (DE)

(73) Assignee: Brainlab AG, Munich (DE)

( * ) Notice: Subject to any disclaimer, the term of this patent is extended or adjusted under 35 U.S.C. 154(b) by 138 days.

(21) Appl. No.: 18/010,514

(22) PCT Filed: Aug. 12, 2020

(86) PCT No.: PCT/EP2020/072561
§ 371 (c)(1),
(2) Date: Dec. 15, 2022

(87) PCT Pub. No.: WO2022/033670
PCT Pub. Date: Feb. 17, 2022

(65) Prior Publication Data
US 2023/0225794 A1    Jul. 20, 2023

(51) Int. Cl.
*A61B 34/10* (2016.01)
*A61B 34/20* (2016.01)
*A61B 90/00* (2016.01)

(52) U.S. Cl.
CPC .............. *A61B 34/10* (2016.02); *A61B 34/20* (2016.02); *A61B 90/39* (2016.02);
(Continued)

(58) Field of Classification Search
None
See application file for complete search history.

(56) References Cited

U.S. PATENT DOCUMENTS

2014/0200621 A1   7/2014  Malackowski et al.
2016/0242858 A1*  8/2016  Moctezuma de la Barrera .......... A61B 34/30
(Continued)

FOREIGN PATENT DOCUMENTS

EP    3212104 A1    9/2017

OTHER PUBLICATIONS

International Search Report dated May 19, 2021 for PCT/EP2020/072561, 17 pages.
(Continued)

*Primary Examiner* — Joel Lamprecht
*Assistant Examiner* — Ashish S Jasani
(74) *Attorney, Agent, or Firm* — Tucker Ellis LLP

(57) ABSTRACT

A computer-implemented method plans a position of a tracking reference device for referencing a position in a medical environment. The method includes a determination of avoidance regions in which a tracking reference device should not be placed so as to safeguard proper tracking of the tracking reference device and/or an instrument tracking reference device which is attached to a medical instrument. The avoidance region is a region lying, from the point of view of a tracking device for tracking the tracking reference device, in the shadow of an envelope surrounding at least one medical instrument. Additionally or alternatively, an avoidance region may lie in between the position of the tracking device and the envelope to avoid a shadowing, by the tracking reference device, of an instrument tracking reference device attached to the medical instrument. Information describing the position of the at least one avoidance region is displayed to a user, and also information about the position of a region which is suitable for placement of the tracking reference device can be displayed to the user.

19 Claims, 5 Drawing Sheets

(52) U.S. Cl.
CPC .................. *A61B 2034/102* (2016.02); *A61B 2034/105* (2016.02); *A61B 2034/107* (2016.02); *A61B 2034/2051* (2016.02); *A61B 2034/2055* (2016.02); *A61B 2034/2068* (2016.02); *A61B 2090/397* (2016.02); *A61B 2090/3983* (2016.02)

(56) References Cited

U.S. PATENT DOCUMENTS

| | | |
|---|---|---|
| 2019/0038362 A1 | 2/2019 | Nash et al. |
| 2020/0100847 A1 | 4/2020 | Siegler et al. |

OTHER PUBLICATIONS

Pfeiffer, et al., A New Module Combining Two Tracking Cameras to Expand the Workspace of Surgical Navigation Systems, Dec. 13, 2016, 6 pages.

* cited by examiner

DETERMINING AN AVOIDANCE REGION FOR A REFERENCE DEVICE

RELATED APPLICATION DATA

This application is a National Phase application of International Application No. PCT/EP2020/072561, filed Aug. 12, 2020, the contents of which are incorporated herein by reference.

FIELD

The present invention relates to a computer-implemented method planning a position of a tracking reference device for referencing a position in a medical environment, a corresponding computer program, a computer-readable storage medium storing such a program and a computer executing the program, as well as a medical system comprising an electronic data storage device and the aforementioned computer.

TECHNICAL BACKGROUND

In navigated medical procedures there exists the problem of requiring a line of sight between reference device comprising markers for defining positions in the patient space and a tracking device which tracks the markers. Conventionally, such a line of sight is safeguarded for example by applying standardized spatial setups. However, such setups are not applicable to arbitrary medical cases.

The present invention has the object of providing an improved way of maintaining a line of sight between a reference device and its associated tracking device.

The present invention can be used for image-guided surgery procedures.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION

In the following, a short description of the specific features of the present invention is given which shall not be understood to limit the invention only to the features or a combination of the features described in this section.

The disclosed method encompasses determination of avoidance regions in which a tracking reference device should not be placed so as to safeguard proper tracking of the tracking reference device and/or an instrument tracking reference device which is attached to a medical instrument. The avoidance region is defined as a region lying, for the point of view of a tracking device for tracking the tracking reference device, in the shadow of an envelope surrounding at least one medical instrument. Additionally or alternatively, an avoidance region may lie in between the position of the tracking device and the envelope to avoid a shadowing, by the tracking reference device, of an instrument tracking reference device attached to the medical instrument. Information describing the position of the at least one avoidance region is displayed to a user, and also information about the position of a region which is suitable for placement of the tracking reference device can be displayed to the user.

GENERAL DESCRIPTION

In this section, a description of the general features of the present invention is given for example by referring to possible embodiments of the invention.

In general, the invention reaches the aforementioned object by providing, in a first aspect, a computer-implemented medical method of planning a position of a tracking reference device for referencing (i.e. defining and/or marking) a position in a medical environment. The position in the medical environment is for example a relative position between the tracking reference device and an anatomical body part of a patient or a relative position between the tracking reference device and a medical device (such as a hand-operated instrument, a robotic arm, or a medical imaging device such as a C-arm, a microscope or a digital camera), or a position of the tracking reference device in a reference system used for defining positions when conducting a navigated medical procedure. The method comprises executing, on at least one processor of at least one computer (for example at least one computer being part of a navigation system), the following exemplary steps which are executed by the at least one processor.

In a (for example first) exemplary step, planning image data is acquired which describes a three-dimensional medical image of an anatomical body part of a patient. The medical image is for example a tomographic image such as a computed x-ray tomography or a magnetic resonance tomography of the anatomical body part. The anatomical body part can be any anatomical body part, for example at least a part of the patient's spine (specifically, a vertebra) or of an extremity of the patient or of the patient's head, for example at least part of the patient's brain, or of the patient's pelvis.

In a (for example second) exemplary step, instrument position data is acquired based on the planning image data, wherein the instrument location data describes a planned position of a medical instrument for using the medical instrument on the anatomical body part. The medical instrument is or comprises for example at least one of an implant or a drill sleeve provided with a further tracking reference device (called instrument tracking reference device) or a drill provided with an instrument tracking reference device or an electric screwdriver provided with an instrument tracking reference device. In such a case, the instrument location data can within the framework of the method according to the first aspect be acquired by detecting a rotational and/or translational movement of the medical instrument using for example a tracking device for tracking the instrument tracking reference device.

In a (for example third) exemplary step, instrument shape data is acquired which describes a three-dimensional shape of the medical instrument. The instrument shape data can be acquired as a predetermined data set for example from a database (for example, from construction data which is for example usable for computer-aided design of the medical instrument) or as user input (for example by manually contouring the envelope in a digital image such as a video or still camera image of the medical instrument or by manually contouring the envelope hands-free).

In a (for example fourth) exemplary step, instrument envelope data is acquired based on the instrument shape data and the instrument position data, wherein the instrument envelope data describes a position and a shape of a three-dimensional envelope around the shape of the instrument. In an example, the medical instrument comprises a plurality of medical instruments and the envelope is a common envelope around the shapes of the plurality of medical instruments. The envelope is determined for example by defining a three-dimensional margin around the shape of the medical instrument having a constant distance around the periphery of the medical instrument. Alternatively, the envelope may be defined as a geometric shape which surrounds the whole of the medical instrument but does not have the same distance to all points on the surface of the medical instrument. For example, the envelope may be defined has a non-cubic box around the medical instrument and/or the position of the medical instrument. For example, the envelope has a regular or an irregular geometry. The envelope is for example defined such that it surrounds the medical instrument along its trajectory when it is used, for example when it is moved relative to the anatomical body part. For example, the medical instrument is a navigated drill and the envelope surrounds the drill along the trajectory of the drill when it is drilled into the anatomical body part.

In a (for example fifth) exemplary step, avoidance region data is determined based on the instrument envelope data, wherein the avoidance region data describes the position of an avoidance region in which the tracking reference device shall not be positioned. The avoidance region may comprise a plurality of spatially disjunct avoidance regions or only a single coherent avoidance region. The envelope described by the envelope data is considered to be a visual obstacle which prevents the tracking device from tracking the tracking reference device if the tracking reference device is located behind the envelope from the perspective of the tracking device. The avoidance region therefore encompasses the space which is shaded by the envelope from the field of view of the tracking device so that the tracking reference device cannot be detected by the tracking device if it is located in the avoidance region. Additionally or alternatively, the avoidance region comprises for example a space lying between the position of the tracking device and the envelope and/or the position of the envelope because the tracking reference device should not be located in that region to avoid hampering detection of the instrument tracking reference device by the tracking device due to tracking reference device shadowing the instrument tracking reference device from the perspective of the tracking device. Additionally or alternatively, the avoidance region comprises the envelope (for example, the volume defined by the envelope). Specifically, the tracking reference device should or must not be positioned within the envelope and/or on its boundary because the volume defined by the envelope should or must be kept free of mechanical interference, for example collisions, between the tracking reference device on the one hand and a medical instrument and/or implant and/or instrument tracking reference device attached to the medical instrument on the other hand. Such an avoidance region lying between the position of the tracking device and the position of the envelope is calculated for example only to extend between the position of the tracking device and a common envelope which is limited to an envelope of all position of markers included in one or more instrument tracking reference devices.

In an example of the method according to the first aspect, reference position data is determined based on the planning image data and the instrument envelope data, wherein the reference position data describes a position of the tracking reference device which does not lie in the avoidance region. The avoidance region constitutes a region in which the position of the tracking reference device described by the reference position data must not lie. The reference position data is determined such that the tracking reference device is visible for a tracking device such as a video camera or infrared-sensitive camera or magnetic tracking sensor when the tracking reference device attains the reference position. For example, the avoidance region represents or is a spatial region which, when viewed from the position of the tracking device, an area which is invisible due to the envelope of the medical instrument. The avoidance region therefore constitutes a region in which the tracking reference device would be invisible to the tracking device if it were placed in the avoidance region and viewed from the position of the tracking device. In an example, the position of the tracking reference device is determined such that is as close as possible to an anatomical target position which it shall reference while not lying in the avoidance region.

In a further exemplary step of the method according to the first aspect, reference device shape data is acquired which describes a three-dimensional shape of the tracking reference device, wherein the reference position data is determined further based on the reference device shape data. For example, the reference position data is determined such that the tracking reference device does not collide with any other device (such as an instrument tracking reference device attached to the medical instrument) or anatomical body part of the patient when the tracking reference device attains the reference position.

In an example of the method according to the first aspect, at least one of the planned position of the medical instrument or the position of the avoidance region is defined in a reference system used for defining positions in the medical image, for example relative to the position of the anatomical body part.

In an example of the method according to the first aspect, tracking device data is acquired which describes a position and a field of view of a tracking device usable for tracking the tracking reference device. The avoidance region data is then determined further based on the tracking device data. For example, the avoidance region data is determined such that the avoidance region does not extend outside the field of view. For example, the avoidance region comprises the field of view as far as it lies between the position of the envelope and the position of the tracking device. For example, the avoidance region comprises the field of view as far as it lies behind the position of the envelope when viewed from the position of the tracking device. For example, the avoidance region is determined by determining, outgoing from the position of the tracking device, a tangential surface on the envelope.

In an example of the method according to the first aspect, the medical instrument comprises or is attached to an instrument tracking reference device comprising a plurality of markers. Then, the method for example comprises a step in which marker plane data is acquired which describes an angle between a marker plane in which the plurality of markers are disposed and a central ray of the field of view of the tracking device. The instrument position data is then determined further based on the marker plane data.

For example, the tracking reference device or the instrument tracking reference device are marker devices comprising a plurality of markers. The markers may be active or passive optical markers such as markers comprising light emitting diodes or having a retroreflective surface, or emitting electromagnetic coils, or magnetic field sensors. For example, the tracking reference device is an electromagnetic reference device comprising for example a coil array as markers, or the tracking reference device is a magnetic field sensor, and a spatial margin is added around the position of the envelope, wherein the margin is defined to be part or is part of the avoidance region so as to avoid electromagnetic interference and/or incompatibility between the tracking reference device and the medical instrument and/or the instrument tracking reference device when the tracking reference device is at the reference position.

In an example of the method according to the first aspect, display data is determined based on the avoidance region data, wherein the display data describes an image rendering of the position of the tracking reference device to be output by a display device. For example, the display data is determined based on the instrument position data, wherein the display data describes an image rendering of the position of the envelope to be output by a display device. Alternatively or additionally, display data is determined based on the avoidance region data, wherein the display data describes an image rendering of the position of the avoidance region to be output by a display device. For example, the display data is output by the display device. For example, the display device comprises a monitor or a light projection device. For example, the display device is included in a head-mounted device.

In a second aspect, the example embodiment is directed to a computer program stored on a non-transient storage medium and comprising instructions that, when the program is executed by at least one processor device of at least one computer, causes the at least one computer to carry out method according to the first aspect.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:
a) the at least one computer according to the fourth aspect, wherein the program, when executed by the at least one computer, causes the computer to carry out the method according to the first aspect as far as it comprises a step of displaying the display data;
b) at least one electronic data storage device storing at least the planning image data and the instrument position data and the instrument shape data and for example the instrument shape data; and
c) the display device,
wherein the at least one computer is operably coupled to
the at least one electronic data storage device for acquiring, from the at least one data storage device, the planning image data and the instrument position data and the instrument shape data and, if the data storage device stores the instrument shape data, the instrument shape data, and
the display device for issuing a control signal to the display device for controlling the display device to display the image rendering described by the display data.

Alternatively or additionally, the invention according to the fifth aspect is directed to a for example non-transitory computer-readable program storage medium storing a program for causing the computer according to the fourth aspect to execute the data processing steps of the method according to the first aspect.

In a sixth aspect, the invention is directed to the use of the system according to the fifth aspect for conducting a medical procedure, wherein the use comprises execution of the steps of the method according to first aspect as far as it comprises a step of displaying the display data for displaying the position of at least one of the avoidance region, the envelope or the medical instrument.

For example, the invention does not involve or in particular comprise or encompass an invasive step which would represent a substantial physical interference with the body requiring professional medical expertise to be carried out and entailing a substantial health risk even when carried out with the required professional care and expertise.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The example embodiment also relates to a computer program stored on a non-transient storage medium and comprising instructions that, when executed by a processor device of a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium, which for example comprises code means which are adapted to perform any or all of the method steps described herein. The example embodiment also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device, also called reference device, can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Throughout the figures, the same reference signs denote the same entities.

Figure 1:
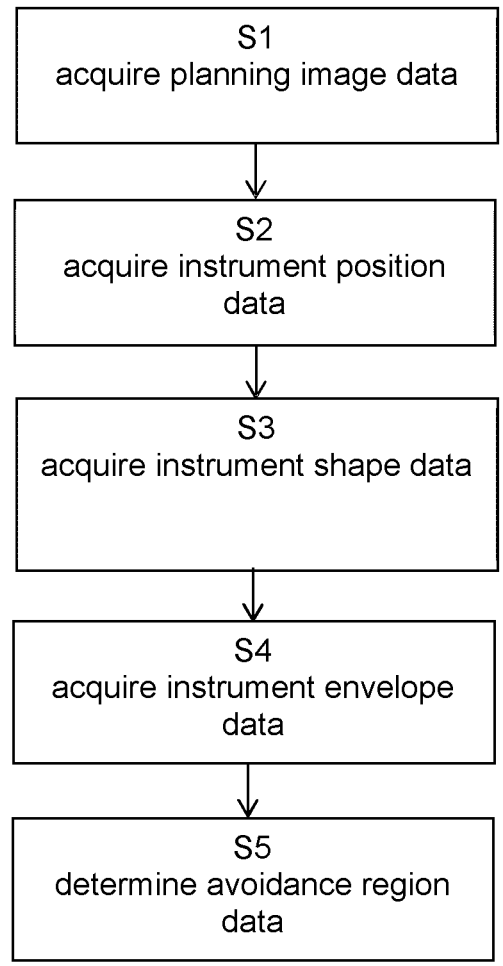
FIG. 1 illustrates the basic steps of the method according to the first aspect.

FIG. 1 illustrates the basic steps of the method according to the first aspect, in which step S1 encompasses acquisition of the planning image data, step S2 encompasses acquisition of the instrument position data and subsequent step S3 encompasses acquisition of the instrument shape data. Step S4 continues with acquisition of the instrument envelope data, and then the avoidance region data is determined in step S5.

Figure 2:
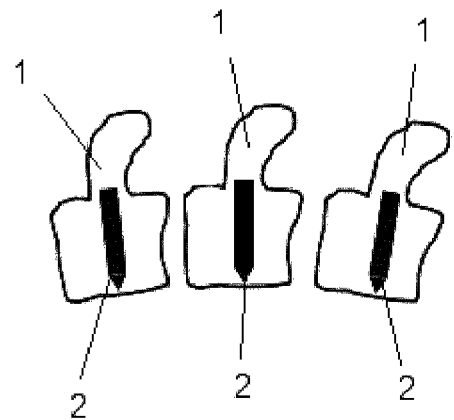
FIG. 2 shows implants placed in an anatomical body parts.

FIG. 2 shows implants 2, for example screws, which are placed in anatomical body parts 1 embodied by vertebrae. The positions of the implants 2 which also determine the paths for inserting the implants 2 or the paths themselves have been predetermined, for example by using image-based planning which may involve atlas-matching of a patient image showing the anatomical body part 1 or running a segmentation algorithm on such a patient image. The segmentation algorithm uses for example artificial intelligence for determining the implantation paths.

Figure 3:
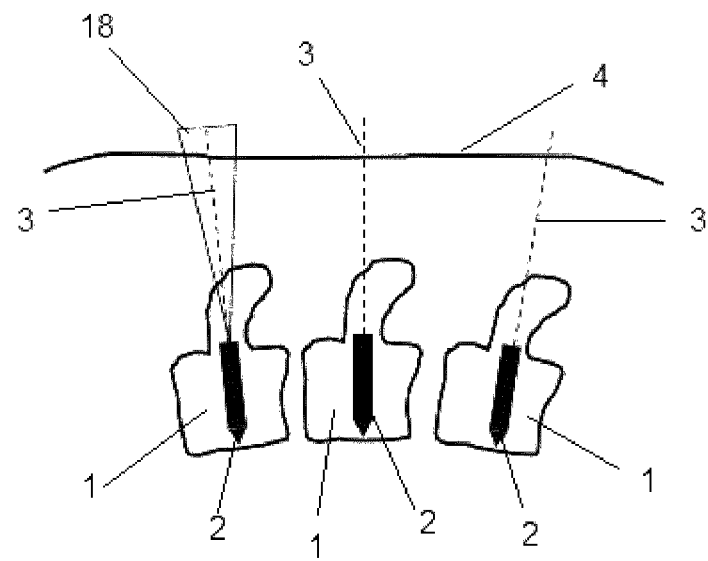
FIG. 3 shows determination of the implantation paths of the implants.

FIG. 3 shows that an implantation cone 18 around the paths 3 are considered to account for the greater deviation from a back projection used for planning the paths 3 with increasing distance from the implant 2. For example, the surface of the skin 4 serves as a starting point for computing the back projection. For example, a rotation of the medical instrument for example by +/−60° around a longitudinal axis of the medical instrument 6 is considered to account for imprecise use of the medical instrument.

Figure 4:
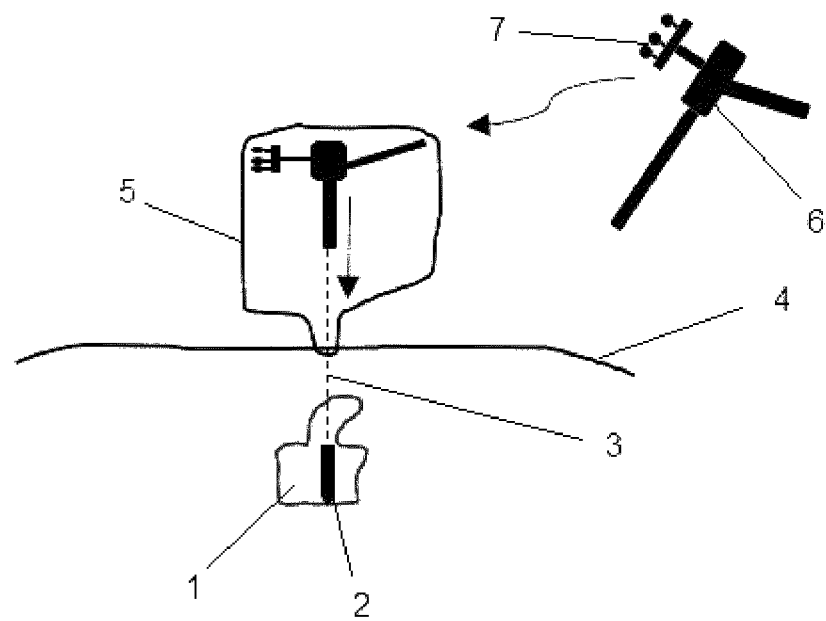
FIG. 4 shows determination of an envelope around a medical instrument which covers the implantation trajectory.

FIG. 4 illustrates that a movement (indicated by the arrow running parallel to the path 3) of the medical instrument 6 embodied by a navigated drill sleeve having a marker device 7 attached to it is planned and that an envelope 5 is determined which surrounds the medical instrument 6 throughout the movement at least as long as at least a part of the medical instrument is disposed outside of the anatomical body part 1.

Figure 5:
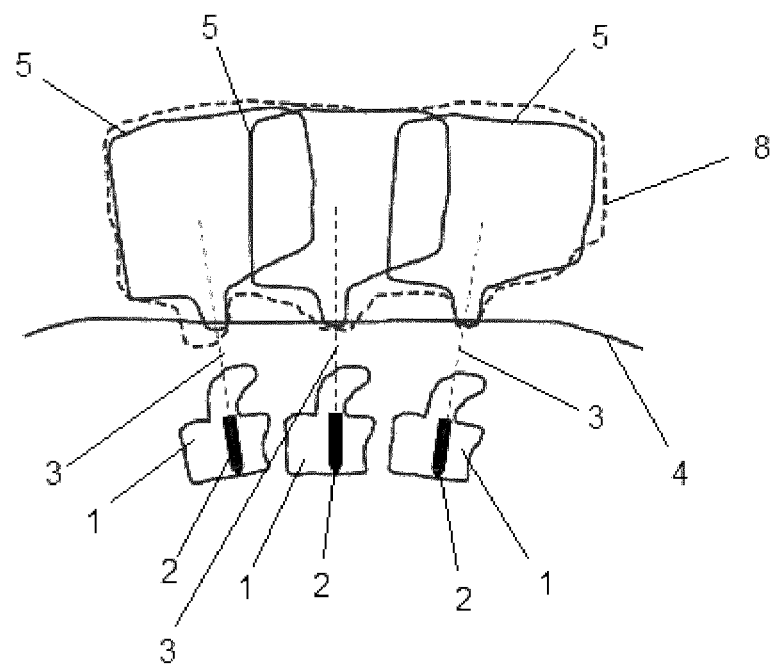
FIG. 5 shows determination of an overall envelope for a plurality of implantation trajectories.

FIG. 5 illustrates determination of an overall envelope or common envelope 8 which surrounds the three individual envelopes 5.

Figure 6:
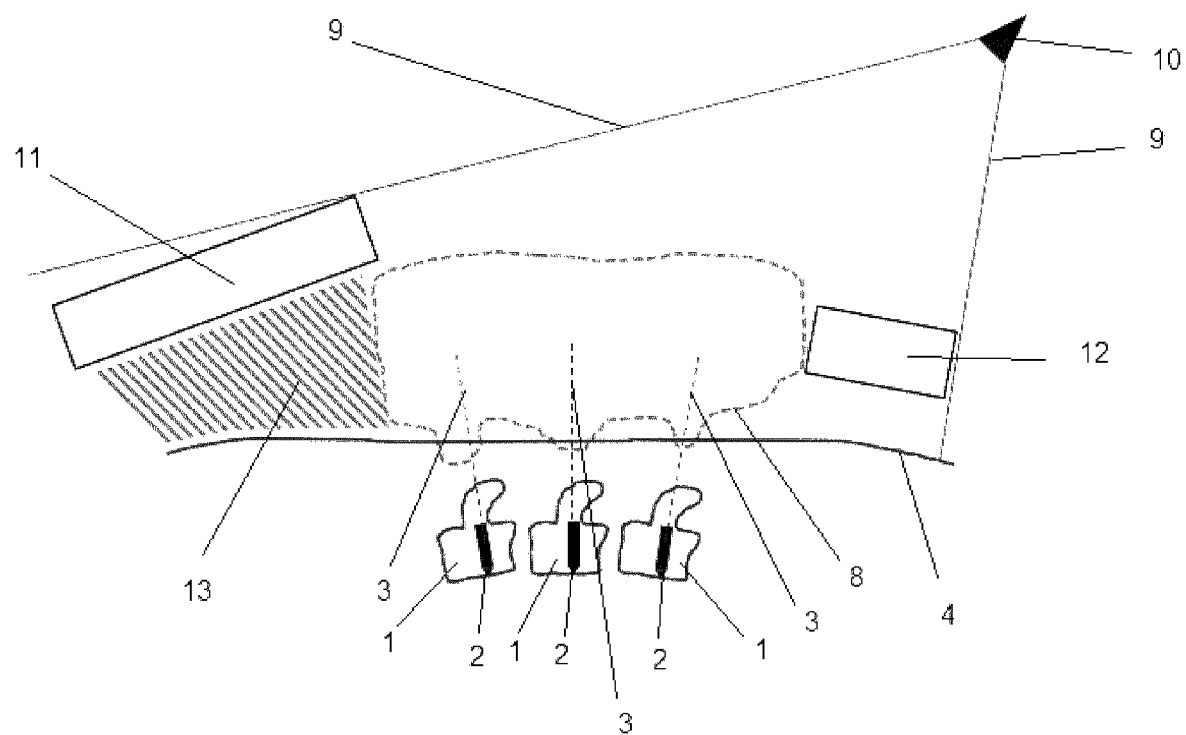
FIG. 6 shows determination of the avoidance region.

FIG. 6 illustrates determination of the avoidance region 13 which is indicated by hatched lines and lies in the shadow of the common envelope 8 when viewed from the position of the tracking device 10 having a conical field of view 9. The avoidance region 13 is defined and/or delimited by at least one tangent from the position of the tracking device onto the envelope. Boxes 11 and 12 indicate regions in which the tracking reference device can be positioned without causing any problem for tracking it or for tracking the instrument tracking reference device. These regions are called for example acceptance regions and can in the framework of the method according to the first aspect also be displayed as visual information to a user. Additionally, an improved or optimal position of the tracking device can also be suggested to the user as displayed visual information.

Figure 7:
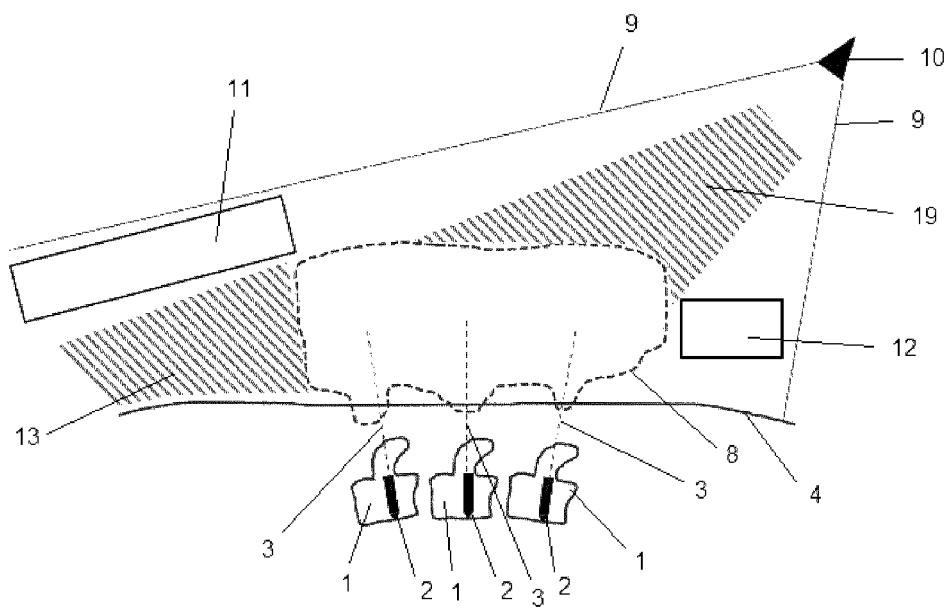
FIG. 7 shows determination of a second avoidance region.

FIG. 7 basically corresponds to FIG. 6 with the additional feature of defining a further avoidance region 19 which is indicated by the hatched lines and lies in between the position of the tracking device 10 and the common envelope 8.

Figure 8:
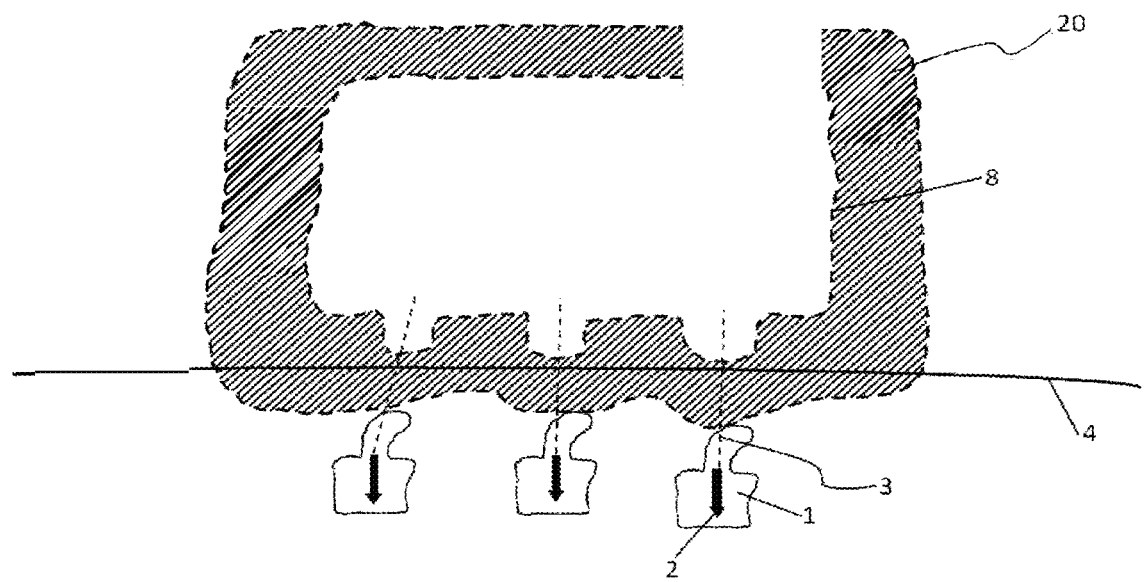
FIG. 8 shows a margin around the avoidance region for the case of electromagnetic tracking.

FIG. 8 illustrates the definition of a margin 20 (specifically, and additional margin) around the common envelope 8 for example in the case of using electromagnetic tracking for tracking the tracking reference device. The margin is for example three-dimensional and represents and additional volume around the common envelope 8 and for example is directly adjacent to the common envelope 8. The margin 20 is defined to be part of the avoidance region 13, 19 and therefore constitutes and additional volume in which the tracking reference device shall not be positioned. For example, the margin 20 serves to keep a minimum distance between the tracking reference device and the medical instrument 6 and/or an instrument tracking reference device 7 to avoid electromagnetic incompatibility effects between the tracking reference device and the medical instrument 6 and/or an instrument tracking reference device 7.

Figure 9:
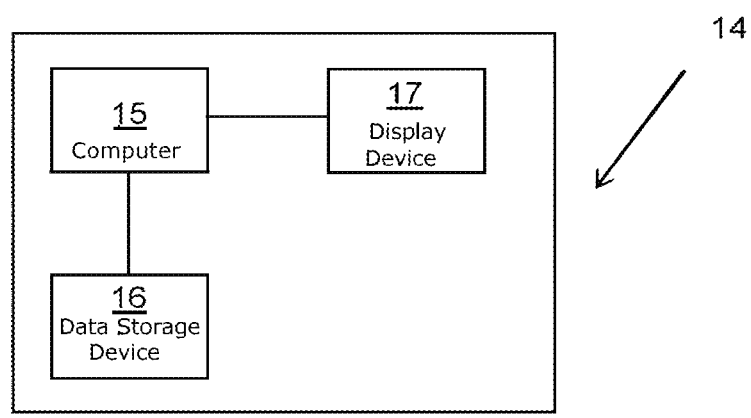
FIG. 9 is a schematic illustration of the system according to the fifth aspect.

FIG. 9 is a schematic illustration of the medical system 14 according to the fifth aspect. The system is in its entirety identified by reference sign 14 and comprises a computer 15, an electronic data storage device (such as a hard disc) 16 for storing at least the patient data and a display device 17 (such as a standard monitor or a touch screen). The components of the medical system 14 have the functionalities and properties explained above with regard to the fifth aspect of this disclosure.

The invention claimed is:

1. A computer-implemented method of planning a position of an associated tracking reference device for referencing a position in a medical environment, the method comprising:

acquiring planning image data that describes a three-dimensional medical image of an anatomical body part of an associated patient;

acquiring instrument position data based on the planning image data, wherein the instrument position data describes a planned position of an associated medical instrument for using the associated medical instrument on the anatomical body part;

acquiring instrument shape data that describes a three-dimensional shape of the associated medical instrument;

acquiring tracking device data that describes a position and a field of view of an associated tracking device usable for tracking the associated tracking reference device;

acquiring instrument envelope data based on the instrument shape data and the instrument position data, wherein the instrument envelope data describes a position and a shape of a three-dimensional envelope around the shape of the associated instrument; and determining avoidance region data based on the instrument envelope data and the tracking device data, wherein the avoidance region data describes a position of an avoidance region in which positioning the associated tracking reference device is to be avoided to maintain a line of sight between the associated tracking device and the associated tracking reference device.

2. The method according to claim 1, further comprising:
determining reference position data based on the planning image data and the instrument envelope data, wherein the reference position data describes a position of the associated tracking reference device that does not lie in the avoidance region.

3. The method according to claim 2, wherein determining the reference position data comprises determining reference position data that describes a position of the associated tracking reference device that is as close as possible to an anatomical target position which it shall reference while not lying in the avoidance region.

4. The method according to claim 2, further comprising:
acquiring reference device shape data that describes a three-dimensional shape of the associated tracking reference device,
wherein determining the reference position data comprises determining the reference position data based on the reference device shape data.

5. The method according to claim 4, wherein acquiring the reference device shape data comprises acquiring reference device shape data that describes a three-dimensional shape of the associated tracking reference device comprising a plurality of markers, wherein the markers are active or passive optical markers comprising light emitting diodes or having a retroreflective surface, or emitting electromagnetic coils or magnetic field sensors.

6. The method according to claim 1, wherein at least one of the planned position of the associated medical instrument and/or the position of the avoidance region is defined in a reference system used for defining positions in the medical image relative to a position of the anatomical body part.

7. The method according to claim 1, wherein acquiring the instrument shape data comprises acquiring instrument shape data that describes a position and a shape of a common envelope around shapes of a plurality of associated medical instruments comprising the associated medical instrument.

8. The method according to claim 1, wherein determining the avoidance region data comprises determining avoidance region data that describes a field of view as far as it lies between the position of the envelope and the position of the associated tracking device.

9. The method according to claim 8, wherein determining the avoidance region data comprises determining avoidance region data that describes a field of view as far as it lies behind the position of the envelope when viewed from the position of the associated tracking device.

10. The method according to claim 8, wherein determining the avoidance region data comprises determining a tangential surface on the envelope outgoing from the position of the associated tracking device.

11. The method according to claim 1, further comprising:
acquiring marker plane data that describes an angle between a marker plane in which a plurality of markers of an associated instrument tracking reference device operatively coupled with the associated medical instrument are disposed and a central ray of the field of view of the associated tracking device,
wherein acquiring the instrument position data further comprises acquiring the instrument position data based on the marker plane data.

12. The method according to claim 1, wherein acquiring the instrument shape data comprises acquiring instrument shape data that describes a three-dimensional shape of an associated medical instrument provided with an instrument tracking reference device and comprising at least one of an implant or a drill sleeve or a drill or an electric screwdriver.

13. The method according to claim 1, wherein:
acquiring the instrument shape data comprises acquiring instrument shape data that describes a three-dimensional shape of an associated medical instrument provided with an instrument tracking reference device and comprising a drill sleeve or a drill or an electric screwdriver; and
acquiring the instrument location data comprises acquiring the instrument location data by detecting a rotational and/or translational movement of the associated medical instrument.

14. The method according to claim 1, wherein acquiring the planning image data comprises acquiring planning image data that describes a three-dimensional medical image of an anatomical body part comprising one or more vertebrae, at least part of the pelvis or at least part of the brain.

15. The method according to claim 1, further comprising:
determining display data based on the avoidance region data, wherein the display data describes an image rendering of the position of the associated tracking reference device to be output by an associated display device; and
displaying the display data on the associated display device.

16. The method according to claim 1, further comprising:
determining display data based on the instrument position data, wherein the display data describes an image rendering of the position of the envelope to be output by an associated display device; and
displaying the display data on the associated display device.

17. The method according to claim 1, further comprising:
determining display data based on the avoidance region data, wherein the display data describes an image rendering of the position of the avoidance region to be output by an associated display device; and
displaying the display data on the associated display device.

18. A non-transient computer readable storage medium storing a computer program comprising instructions that, when executed by a processor device of an associated computer, cause the associated computer to carry out a method comprising:
acquiring planning image data that describes a three-dimensional medical image of an anatomical body part of an associated patient;
acquiring instrument position data based on the planning image data, wherein the instrument position data describes a planned position of an associated medical instrument for using the associated medical instrument on the anatomical body part;
acquiring instrument shape data that describes a three-dimensional shape of the associated medical instrument;
acquiring tracking device data that describes a position and a field of view of an associated tracking device usable for tracking the associated tracking reference device;
acquiring instrument envelope data based on the instrument shape data and the instrument position data, wherein the instrument envelope data describes a position and a shape of a three-dimensional envelope around the shape of the associated instrument; and
determining avoidance region data based on the instrument envelope data and the tracking device data, wherein the avoidance region data describes a position of an avoidance region in which positioning the associated tracking reference device is to be avoided to maintain a line of sight between the associated tracking device and the associated tracking reference device.

19. A medical system, comprising:
a computer comprising a processor device and a non-transient memory device storing a program thereon, the program when executed by the processor device, causes the computer to carry out a method of planning a position of an associated tracking reference device for referencing a position in a medical environment;
at least one electronic data storage device operatively coupled with the computer, the at least one electronic data storage device storing planning image data, instrument position data, and instrument shape data; and
a display device operatively coupled with the computer, wherein the at least one computer is operable to
acquire, from the at least one data storage device, the planning image data, the instrument position data, the instrument shape data, and, if the at least one electronic data storage device stores the instrument shape data, the instrument shape data, and
issue a control signal to the display device for controlling the display device to display an image rendering described by display data,
wherein the program when executed by the processor device causes the computer to perform a method comprising:
acquiring planning image data that describes a three-dimensional medical image of an anatomical body part of an associated patient;
acquiring instrument position data based on the planning image data, wherein the instrument position data describes a planned position of an associated medical instrument for using the associated medical instrument on the anatomical body part;
acquiring instrument shape data that describes a three-dimensional shape of the associated medical instrument;
acquiring tracking device data that describes a position and a field of view of an associated tracking device usable for tracking the associated tracking reference device;
acquiring instrument envelope data based on the instrument shape data and the instrument position data, wherein the instrument envelope data describes a position and a shape of a three-dimensional envelope around the shape of the associated instrument;
determining avoidance region data based on the instrument envelope data and the tracking device data, wherein the avoidance region data describes a position of an avoidance region in which positioning the associated tracking reference device is to be avoided to maintain a line of sight between the associated tracking device and the associated tracking reference device; and
determining the display data based on one or more of:
the avoidance region data, wherein the display data describes the image rendering of the position of the associated tracking reference device to be output by the display device based on the control signal;
the instrument position data, wherein the display data describes the image rendering of the position of the envelope to be output by the display device based on the control signal; and/or
the avoidance region data, wherein the display data describes the image rendering of the position of the avoidance region to be output by the display device based on the control signal.

* * * * *